US012569590B2

(12) United States Patent
Geuna et al.

(10) Patent No.: US 12,569,590 B2
(45) Date of Patent: Mar. 10, 2026

(54) MEDICAL DEVICE COMPRISING A CHITOSAN-BASED SUPPORT STRUCTURE

(71) Applicants: Università degli Studi di Torino, Turin (IT); MONARCH BIOIMPLANTS GmbH, Root D (CH)

(72) Inventors: Stefano Geuna, Orbassano (IT); Francesco Porpiglia, Orbassano (IT); Thomas Freier, Mainz (DE)

(73) Assignees: Università degli Studi di Torino, Turin (IT); Monarch Bioimplants GmbH, Root D (CH)

( * ) Notice: Subject to any disclaimer, the term of this patent is extended or adjusted under 35 U.S.C. 154(b) by 1117 days.

(21) Appl. No.: 17/595,642

(22) PCT Filed: May 18, 2020

(86) PCT No.: PCT/IB2020/054677
§ 371 (c)(1),
(2) Date: Nov. 19, 2021

(87) PCT Pub. No.: WO2020/234740
PCT Pub. Date: Nov. 26, 2020

(65) Prior Publication Data
US 2022/0218870 A1      Jul. 14, 2022

(30) Foreign Application Priority Data
May 22, 2019      (IT) ........................ 102019000007115

(51) Int. Cl.
A61L 27/26      (2006.01)
A61L 27/54      (2006.01)
(Continued)

(52) U.S. Cl.
CPC ............... A61L 27/26 (2013.01); A61L 27/54 (2013.01); A61L 27/58 (2013.01); C08L 5/08 (2013.01)

(58) Field of Classification Search
None
See application file for complete search history.

(56) References Cited

U.S. PATENT DOCUMENTS 5,695,857 A      12/1997   Burrell et al.
8,337,386 B2     12/2012   Madden
(Continued)

FOREIGN PATENT DOCUMENTS

EP      3 266 467      1/2018
WO     2008/072230     6/2008

OTHER PUBLICATIONS

Wang, Y. C., & Ho, C. (2004). Micropatterning of proteins and mammalian cells on biomaterials. The FASEB Journal, 18(3), 525-527. https://doi.org/10.1096/fj.03-0490fje (Year: 2004).*
(Continued)

*Primary Examiner* — Charles A Marmor, II
*Assistant Examiner* — Marc D. Honrath
(74) *Attorney, Agent, or Firm* — Nixon & Vanderhye P.C.; Lars H. Genieser

(57)      ABSTRACT

Medical device (10) having a film support structure (12), the film support structure comprising a composition containing chitosan, the film support structure (12) including a surface sculpturing (14). The surface sculpturing (14) comprises a plurality of peaks (16) and troughs (18) defining a plurality of grooves, the peaks (16) having a peak width (PW) ranging from 0.1 to 1000 μm, preferably 1 to 100 μm, the troughs have a trough width (TW) ranging from 0.1 to 1000 μm, preferably 1 to 100 μm, wherein a peak to trough distance (D) ranges from 0.1 to 1000 μm.

13 Claims, 5 Drawing Sheets

(51) Int. Cl.
  A61L 27/58   (2006.01)
  C08L 5/08    (2006.01)

(56)      References Cited

U.S. PATENT DOCUMENTS

| | | |
|---|---|---|
| 10,207,022 B2 | 2/2019 | Montenegro |
| 2013/0204078 A1 | 8/2013 | Li et al. |
| 2020/0048611 A1* | 2/2020 | Crone .................. C12N 5/0068 |
| 2021/0060203 A1* | 3/2021 | McCarthy ......... A61F 13/01012 |
| 2024/0216571 A1* | 7/2024 | Clare .................. A61L 24/0036 |

OTHER PUBLICATIONS

International Search Report for PCT/IB2020/054677 mailed Jul. 6, 2020, 5 pages.
Written Opinion of the ISA for PCT/IB2020/054677 mailed Jul. 6, 2020, 6 pages.
Patel et al., "Dehydrated Human Amnion/Chorion Membrane Allograft Nerve Wrap Around the Prostatic Neurovascular Bundle Accelerates Early Return to Continence and Potency Following Robot-assisted Radical Prostatectomy: Propensity Score-matched Analysis", *European Urology*, vol. 67, Jan. 12, 2015, pp. 977-980.
Piao et al., "Therapeutic Effect of Adipose-Derived Stem Cells and BDNF-immobilized PLGA Membrane in a Rat Model of Cavernous Nerve Injury", Dept. of Urology, The Catholic University of Korea, 2012, 12 pages.

\* cited by examiner

MEDICAL DEVICE COMPRISING A CHITOSAN-BASED SUPPORT STRUCTURE

This application is the U.S. national phase of International Application No. PCT/IB2020/054677 filed May 18, 2020 which designated the U.S. and claims priority to IT patent application No. 102019000007115 filed May 22, 2019, the entire contents of each of which are hereby incorporated by reference.

FIELD OF THE INVENTION

The present disclosure relates in general to a medical device comprising a chitosan-based film support structure for use in prostatectomy surgery.

BACKGROUND OF THE INVENTION

Prostate cancer is the most common cancer among European and American men. Treatment of prostate cancer commonly involves surgical therapy including radical prostatectomy. However, despite the increasing use of nerve-sparing techniques, such as robot-assisted surgery, urinary incontinence and erectile dysfunction remain major adverse consequences of radical prostatectomy.

Cavernous nerve injury caused by different factors, including mechanical traction damage to the neurovascular bundle during mobilization of the prostate, as well as post-operative inflammation of the neurovascular bundle, is the main reason for post-surgical erectile dysfunction.

Modern surgery focuses on nerve-sparing techniques which results in an increased restoration of erectile function by preserving the integrity of the neurovascular bundles.

While mechanical damage to the neurovascular bundle can be minimized by the experienced surgeon, the post-surgical inflammation remains a problem leading to nerve damage, which has to be addressed by advanced materials or structures for nerve repair.

For example, a biodegradable polyester membrane containing brain-derived neurotrophic factor and adipose-derived stem cells has been tested in a rat cavernous nerve crush injury model, and an improved erectile function was observed compared to the non-cell containing group (Piao et al., "Therapeutic effect of adipose-derived stem cells and BDNF-immobilized PLGA membrane in a rat model of cavernous nerve injury", J Sex Med 2012, 9, 1968).

The application of growth factors and anti-inflammatory substances to preserve and regenerate the prostatic neurovascular bundle has been further advanced by the use of dehydrated human amnion/chorion membranes as source of neurotrophic factors and cytokines (Patel et al., "Dehydrated human amnion/chorion membrane allograft nerve wrap around the prostatic neurovascular bundle accelerates early return to continence and potency following robot-assisted radical prostatectomy: propensity score-matched analysis", Eur Urol 2015, 67, 977).

The manufacture process and the regulatory approval and commercialization of medical devices in combination with growth factors and cellular components can be demanding and expensive processes.

Simple technical solutions, preferably based on biocompatible and biodegradable components, and capable of supporting faster recurrence of continence in patients following prostatectomy are continuously investigated. Document EP 3 266 467 A1, for example, discloses a composition comprising chitosan capable of ameliorating the outcome of the radical prostatectomy. Improved technical solutions, however, are still needed in order to further facilitate nerve repair and efficiently support early return of continence and potency in patients following prostatectomy.

SUMMARY OF THE INVENTION

The object of the present disclosure is to provide a medical device capable of achieving an early increase in sexual potency and continence recovery after prostatectomy without inducing any adverse effects.

The above object is achieved thanks to the subject matter recalled specifically in the ensuing claims, which are understood as forming an integral part of this disclosure.

According to the instant disclosure, the above object is achieved by a medical device having a film support structure comprising a composition containing chitosan, the film support structure including a surface sculpturing comprising a plurality of peaks and troughs defining a plurality of grooves, wherein i) peaks have a width ranging from 0.1 to 1000 μm, ii) troughs have a width ranging from 0.1 to 1000 μm, and iii) the distance between a peak and a trough ranges from 0.1 to 1000 μm.

In one or more embodiments, the medical device comprising a chitosan-based support structure herein disclosed is intended for a surgical application, specifically for being applied in contact with the prostatic neurovascular bundle of the subject undergoing prostatectomy.

Moreover, herein disclosed is a method for protecting a prostatic neurovascular bundle of a subject, wherein the medical device comprising a chitosan-based support structure is applied in contact with the prostatic neurovascular bundle of the subject undergoing prostatectomy.

BRIEF DESCRIPTION OF THE DRAWINGS

One or more embodiments will now be described, purely by way of non-limiting example, with reference to the annexed drawings, in which.

DETAILED DESCRIPTION

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

The instant description concerns a medical device having a film support structure comprising a composition containing chitosan for use in preventing and/or treating impotence in a subject undergoing prostatectomy, preferably radical prostatectomy.

Figure 1:
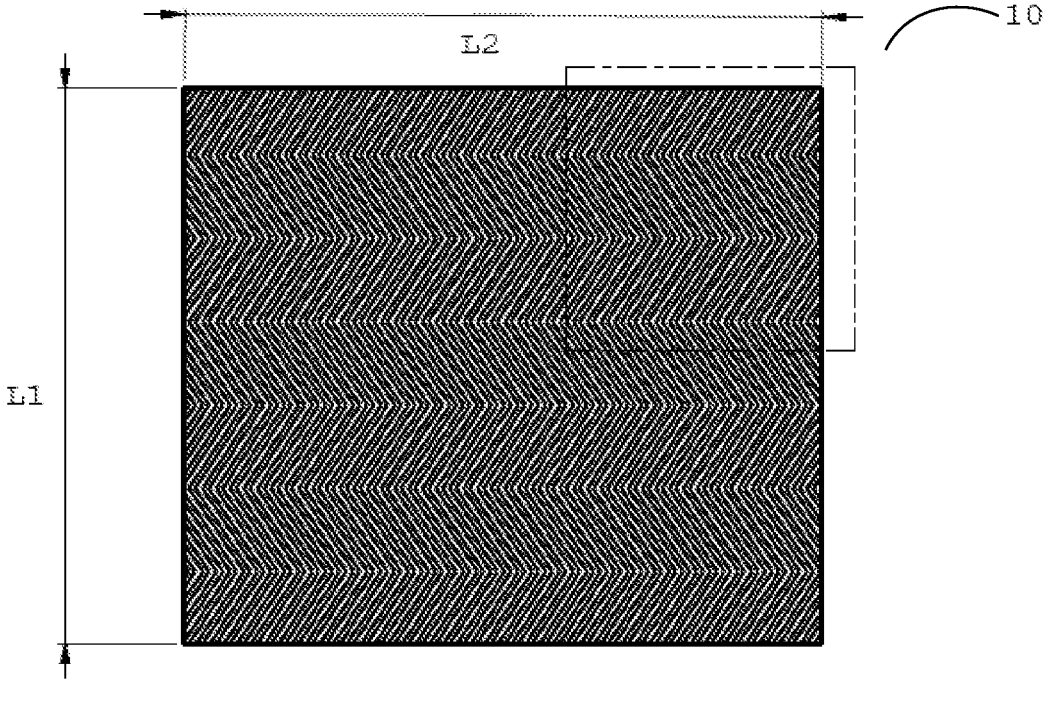
FIG. 1 is a schematic view of a device according to embodiments of the present disclosure.

FIG. 1 shows one embodiment of the medical device object of the present description, indicated by reference number 10.

The medical device 10 has a film support structure comprising a composition containing chitosan, as disclosed in the following.

The film support structure 12 includes a surface sculpturing 14 including a plurality of peaks 16 and troughs 18 defining a plurality of grooves.

In one or more embodiments, the surface sculpturing 14 may comprise straight lines of parallel grooves.

Figure 3:
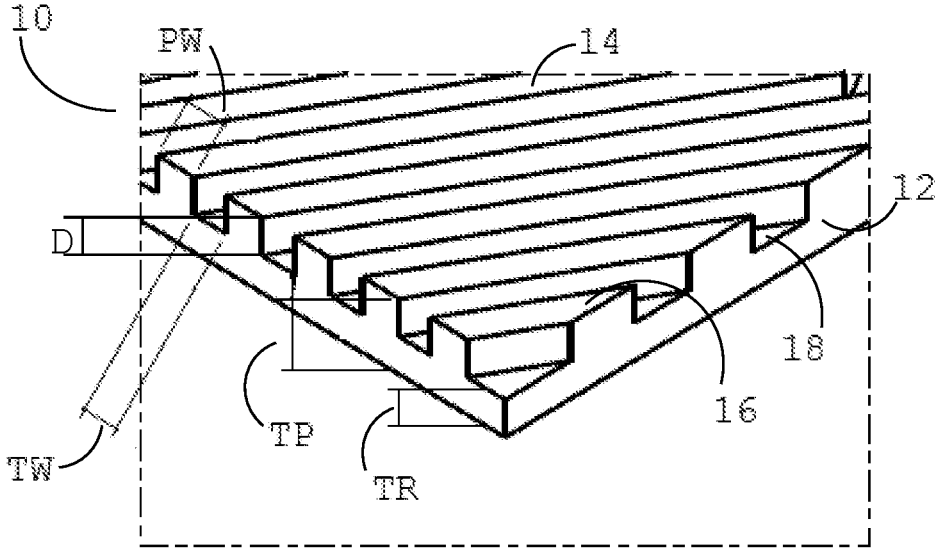
FIG. 3 is a perspective view of a device according to embodiments wherein a detail of the structure is further enlarged.

As shown in FIG. 3, according to the present description a "peak" is a feature of the geometry that sticks out (or in general protrudes) from a reference surface. Because the surface sculpturing is made of a pattern of peaks and troughs, the reference surface the peaks stick out of or protrude from is the trough (bottom) surface.

Examples of the structure of peaks and troughs are clearly shown in FIG. 3, which is an enlarged schematic view of a detail of the medical device 10.

Peaks 16 have a peak width PW ranging from 0.1 to 1000 µm, preferably 1 to 100 µm. Troughs 18 have a trough width TW ranging from 0.1 to 1000 µm, preferably 1 to 100 µm.

In one or more embodiments, peaks 16 and troughs 18 may have a length L ranging from 1 to 100000 µm, preferably 10 to 1000 µm, more preferably 50 to 250 µm. The length L is measured along a direction orthogonal to the direction along which the width is measured. For instance, the length L is measured along a direction parallel to the extension direction of a peak (or a trough), which is orthogonal to the peak (or trough) width.

A peak to trough distance D is comprised between 0.1 to 1000 µm, preferably between 0.5 to 100 µm, more preferably between 1 to 50 µm, wherein the peak to trough distance is measured between an outermost edge or point of a peak (top) surface and an innermost edge or point of a trough (bottom) surface, and along a direction orthogonal to said peak (or trough) width and to said length. For instance, the bundle of directions along which length L, peak width PW and trough width TW are measured allows the identification of a plane to which the direction of distance D is orthogonal (e.g. plane XY for PW, TW, L, and axis Z for distance D in an orthogonal X-Y-Z reference system).

In a preferred embodiment, the thickness of the film support structure 12 at a peak TP may range from 0.2 to 2000 µm, preferably from 1 to 200 µm. The thickness of the film support structure at a through TR may range from 0.1 to 1000 µm, preferably from 0.5 to 100 µm Reference points for thickness measurement are the outermost edge or point of a peak (top) surface and the film surface opposite to the sculptured surface for thickness TP, and the innermost edge or point of a trough (bottom) surface and—again—the film surface opposite to the sculptured surface for thickness TR. Over the film, the following relationship applies at each point thereof: D=TP−TR.

In one or more embodiments, the film support structure 12 is a quadrangular film, as for example shown in FIG. 1, having a first dimension L1 ranging from 1 to 100 mm, preferably 5 to 50 mm and a second dimension L2 ranging from 1 to 100 mm, preferably 5 to 50 mm.

In one or more embodiments, the grooves of the surface sculpturing 14 may be arranged according to a chevron (or V-shaped) pattern.

Figure 2:
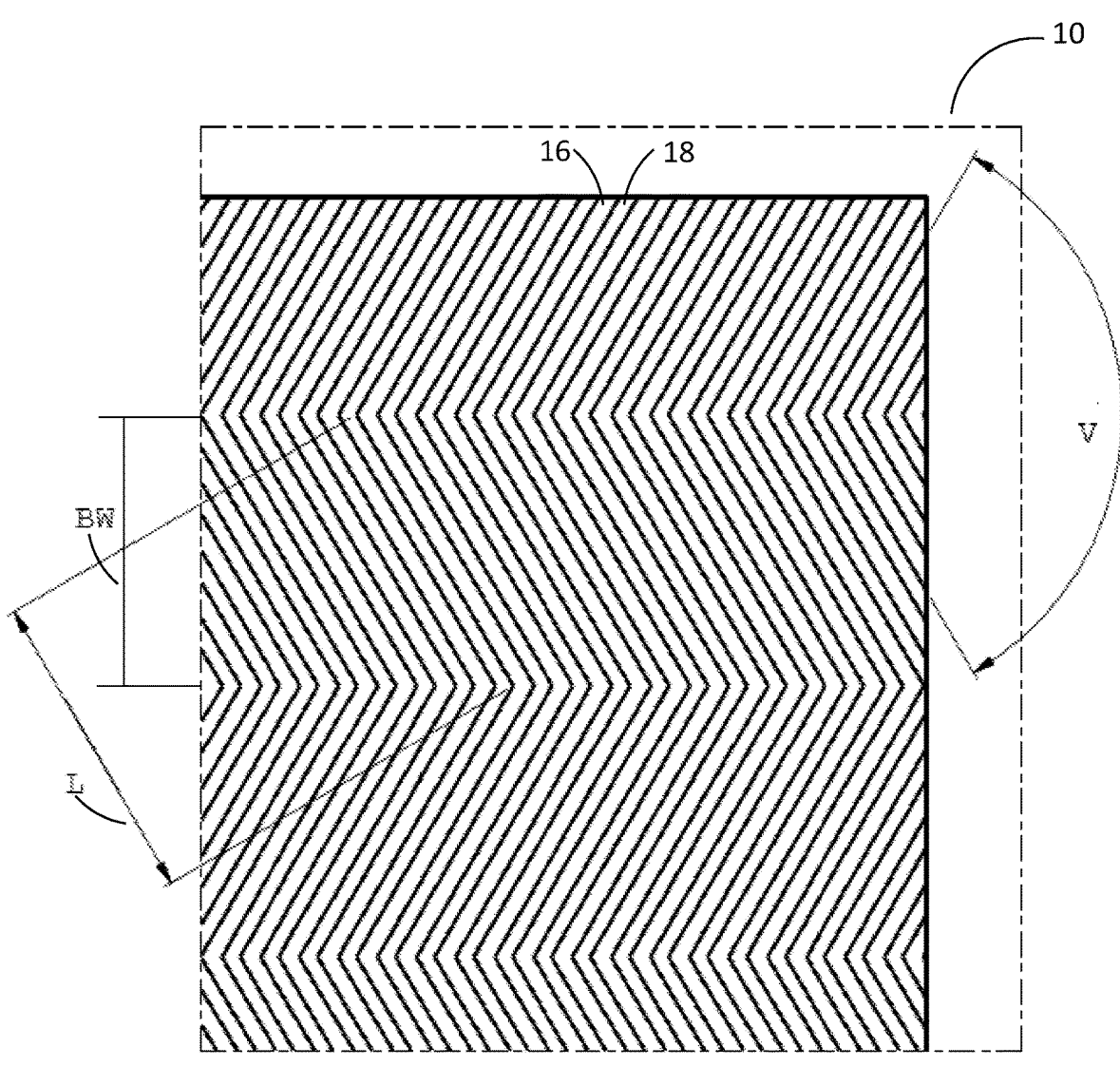
FIG. 2 is an enlarged view of the detail shown in FIG. 1 by discontinuous lines.

As it can be appreciated especially in FIG. 2, the chevron pattern of grooves of the surface sculpturing 14 has a V-angle V less than 180 degrees, preferably 30 to 150 degrees, more preferably 90 to 120 degrees.

The V-angle is the angle comprised between adjacent and incident features (peaks and troughs or grooves equivalently) of the chevron pattern.

In addition, a band width BW of the chevron pattern of the surface sculpturing 14 is 100000 µm or less, preferably ranging from 10 to 1000 µm, more preferably 50 to 250 µm.

By the term "band width" it is meant to designate the transverse dimension of a band-wise domain that encloses an ordinate pattern of parallel, diagonal features of the geometry of the surface sculpturing, the ordinate pattern defining in turn half (or in general a portion featuring peaks and troughs having the same orientation) of a chevron (or V-shaped) pattern.

Alternative embodiments may apply, which are not specifically illustrated in the figures, wherein the pattern of grooves defined by peaks 16 and troughs 18 is other than a chevron pattern, for instance patterns of straight grooves, or patterns in the form of pillars and or cones.

The Inventors of the instant application surprisingly found that by virtue of its particular geometry and chemical composition, the medical device 10 herein disclosed is highly effective in obtaining a favourable outcome of the radical prostatectomy.

Concerning the chemical composition, the medical device 10 has a film support structure 12 characterized by a precise selection of the constituent polymer, which is chitosan.

In the experimental part that follows, the preparation of a specific embodiment of the medical device 10 is disclosed; the device resulted in being effective in the applications concerned.

In one or more embodiments, a high biocompatibility and bioactivity of the medical device 10 may be obtained by using chitosan in form of native chitosan.

In the context of the present disclosure, the expression "native chitosan" refers to the chemical structure of chitosan, i.e. a poly(N-acetyl-D-glucosamine-co-D-glucosamine) copolymer or a poly(D-glucosamine) homopolymer.

Any cross-linked or otherwise chemically modified chitosan is considered a chitosan derivative, having different properties than native chitosan. Cross-linking of chitosan, either ionically or covalently, may lead to the blockage of active functionalities of the biomaterial, namely the amine group.

In the context of the present disclosure the term "native chitosan" includes both the chitosan base and chitosan in form of a chitosan salt.

In one or more embodiments, the film support structure 12 of the medical device 10 comprises a composition containing chitosan, preferably chitosan base, in an amount at least 50%, more preferably at least 90%, more preferably at least 95% by weight (w/w) of the composition, based on the non-aqueous components of the composition.

The film support structure 12 of the medical device may comprise a composition comprising chitosan, preferably chitosan base, in an amount 50% or less, more preferably 10% or less, more preferably 95% or less by weight (w/w) of the composition, based on the non-aqueous components of the composition.

In one or more embodiments, the composition may comprise chitosan either in form of a base and in form of a chitosan salt. Preferably, the composition comprises at least one chitosan salt in an amount of 50% or less, more preferably 10% or less, more preferably 5% or less by weight (w/w) related to the total weight of chitosan.

The presence of chitosan in form of a salt can allow a good adhesion of the medical device 10 herein disclosed to the neurovascular bundle thus avoiding a premature detachment from the site of implantation. The chitosan salt is soluble in an aqueous solvent or physiological medium of neutral pH. Thus, wet tissue can etch the film support structure 12 of the medical device 10 providing for a durable contact with the prostatic neurovascular bundle.

In one or more embodiments, chitosan salts may be derived from the dissolution of chitosan in an aqueous solution of one or more inorganic acids, such as hydrochloric acid, and/or organic acids selected from the group consisting of monobasic or multibasic organic acids having from 2 to 12 carbon atoms and a first pKa value between 1 and 5, such as for example acetic acid, citric acid, lactic acid, malic acid, succinic acid, mandelic acid, oxalic acid, tartaric acid, ascorbic acid, etc.

In one or more embodiments, chitosan may be present in the composition in form of a chitosan base.

In one or more embodiments, the composition of the film support structure 12 of the medical device 10 consists of chitosan, preferably native chitosan.

In one or more embodiments, the composition comprises chitosan with a degree of acetylation of 40% or less, preferably 20% or less, more preferably 10% or less.

In one or more embodiments, the composition comprising chitosan herein disclosed is essentially free of toxic compounds.

In one or more embodiments, the composition of the film support structure 12 of the medical device 10 comprises glycerol in addition to chitosan, preferably in an amount between 1 and 10% by weight, based on the non-aqueous components of the composition.

In one or more embodiments, the composition of the film support structure 12 of the medical device 10 comprises other than chitosan also at least one polymer selected in the group consisting of synthetic polyesters, preferably homopolymers and copolymers based on glycolide, L-lactide, D,L-lactide, p-dioxanone, ε-caprolactone, natural polyesters, preferably from the group of the polyhydroxyalkanoates, such as homopolymers and copolymers based on 3-hydroxybutyrate, 4-hydroxybutyrate, 3-hydroxyvalerate, 3-hydroxyhexanoate, 3-hydroxyoctanoate; polyorthoesters; polycarbonates; polyanhydrides; polyurethanes; polyphosphazenes; polyphosphoesters; polysaccharides; polypeptides; as well as derivatives, copolymers, and blends based on the abovementioned and any other group of bioresorbable polymers.

Other suitable polymers include those, which may be dissolved under physiological conditions, such as homopolymers or copolymers based on vinyl alcohol, vinyl acetate, N-vinyl pyrrolidone, ethylene glycol, propylene glycol, polysaccharides, polypeptides, as well as derivatives, copolymers, and blends based on the aforementioned and any other group of biodissolvable polymers or combinations of biodegradable and biodissolvable polymers.

Other suitable polymers include those selected from the groups of non-biodegradable and non-biodissolvable polymers, as well as their derivatives, copolymers, and blends, including combinations with biodegradable and biodissolvable polymers.

In one or more embodiments, the film support structure 12 of the medical device 10 herein disclosed may further comprise other components, such as for example at least one pharmaceutically active and/or bioactive constituent.

In one or more embodiments, bioactive constituents may be selected from the group consisting of proteins, peptides, nucleic acids, low molecular weight drugs, such as antibiotics or anti-inflammatory drugs, phosphodiesterase inhibitors, agonists or antagonists of the innate immune system, stimulating or differentiating growth factors for stimulating or differentiating growth of at least one cell sub-type, and mixtures thereof.

In one or more embodiments, the film support structure 12 of the medical device 10 may further comprise biological cells, such as for example adipose-derived stem cells (ADSC) and induced pluripotent stem cells (iPSC).

The medical device 10 herein disclosed is intended for a surgical application, specifically for application on the prostatic neurovascular bundle of a subject undergoing prostatectomy.

In one or more embodiments, the film support structure 12 of the medical device 10 is preferably in form of a solid film or a gel-like film.

In one or more embodiments, the film support structure 12 may be in the form of a freeze-dried or solvent-dried film.

In one or more embodiments, the film support structure 12 may be present in form of a flexible film, which may be continuous or interrupted (e.g. perforated).

In one or more embodiments, the medical device 10 further comprises an additional film support structure 12 containing a composition comprising chitosan or another polymer or polymeric composition selected from the group of biodegradable/biodissolvable, or non-biodegradable/non-biodissolvable polymers.

In one or more embodiments, the composition of the film support structure 12 may further comprise at least one pharmaceutically active and/or bioactive constituent or biological cells.

In one or more embodiments, the film support structure 12 of the medical device can have a thickness of 1000 µm or less, preferably 100 µm or less, more preferably 10 µm or less.

The support structure of the medical device subject of the present invention may for example be prepared by means of the following preparation techniques: laser etching, e-beam etching, plasma etching, 3D printing, electrospinning, photolithography, stereolithography, and soft lithography.

In one or more embodiments, the medical device 10 herein disclosed may be applied on the prostatic neurovascular bundle of a subject.

The medical device 10 may present a thickness comprised between 0.2 to 2000 µm at a peak TP and between 0.1 to 1000 µm at a through TR.

In one or more embodiments, the surface area of the medical device 10 may be comprised in the range between and 100 cm², preferable between 5 and 25 cm², more preferably between 5 and 15 cm².

Such a surface area allows covering the prostatic neurovascular bundle completely or partially and, preferably some of the surrounding tissue.

In one or more embodiments, the composition of the film support structure 12 herein disclosed may have a water uptake capacity of less than 100%, preferably comprised between 25% and 80% by weight, more preferably between 50% and 75%.

In one or more embodiments, the film support structure 12 may contain at least one hole (opening) extending through all the thickness of the device, which allows absorption and diffusion of physiological liquids and fast fluid exchange through the film bulk structure.

The at least one hole may have a diameter size of 1000 μm or less, more preferably 500 μm or less, more preferably 250 μm or less. In a preferred embodiment, the at least one hole may have a diameter size of 1 μm or more, preferably 10 μm or more, more preferably 100 μm or more. In one or more embodiments, the diameter size of the holes of the film is between 100 μm and 250 μm.

In one or more embodiments, the holes may cover an area of 50% or less of the film surface, more preferably 10% or less, more preferably 1% or less.

In one or more embodiments, a preferred flow rate of physiological fluids through the chitosan composition in form of a film containing holes is 0.001 ml/min/cm² or more, preferably 0.01 ml/min/cm² or more, more preferably 0.1 ml/min/cm² or more.

Thanks to this property, the accumulation of fluid underneath the composition during implantation can be reduced or prevented thus favouring its adherence to the neurovascular bundle.

In one or more embodiments, the medical device 10 is transparent. Advantageously, this can make it easier for a physician to inspect the application to the neurovascular bundle.

In one or more embodiments, the medical device 10, once applied at the surgical site, may be sutured.

Advantageously, this property allows the fixation of the medical device to the surgical site and prevents dislodgement from the neurovascular bundle. In one or more embodiments, the suture retention strength based on a Prolene USP 6/0 suture and evaluated by a mechanical tester is 0.05 N or more, preferably 0.5 N or more when measured in the dry state, and 0.01 N or more, preferably 0.1 N or more when measured in the wet state.

The medical device subject of the present invention may for example be prepared by means of the following preparation techniques: solvent casting, molding, 3D printing, electrospinning.

Thanks to the specific combination of the particular geometric characteristics and chemical composition the medical device 10 herein disclosed has been found to be surprisingly effective in the recovery of potency and continence after prostatectomy.

The medical device 10 is able to improve the regeneration and repair of nerves specifically important for achieving a faster recurrence of potency and a reduced rate of erectile dysfunction in a subject who undergoes radical prostatectomy. In addition, the medical device 10 allows a faster recurrence of continence and a reduced rate of incontinence.

Moreover, thanks to the biocompatibility and to the antimicrobial and haemostatic properties of chitosan, inflammation, infection and bleeding time reduction can also be achieved. The medical device herein disclosed has the further advantage of reducing the risk of infections thanks to the antibacterial properties of chitosan.

The following examples are provided for purely illustrative purposes and should not be interpreted in a limiting sense in any way of the scope of the invention as defined by the attached claims.

EXAMPLE 1

Preparation of a Composition Comprising Chitosan

1H NMR Spectroscopy

Figure 4:
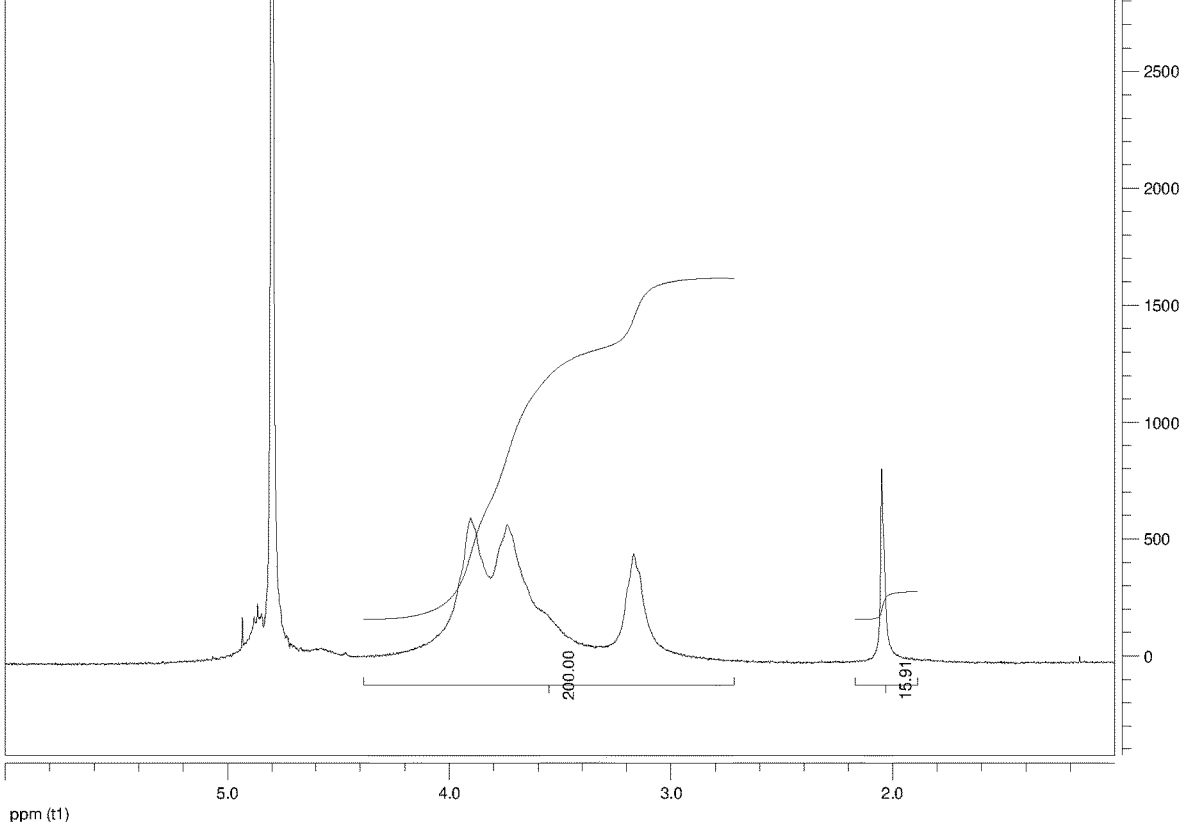
FIG. 4: 1H NMR spectrum of native chitosan as purchased.
Figure 5:
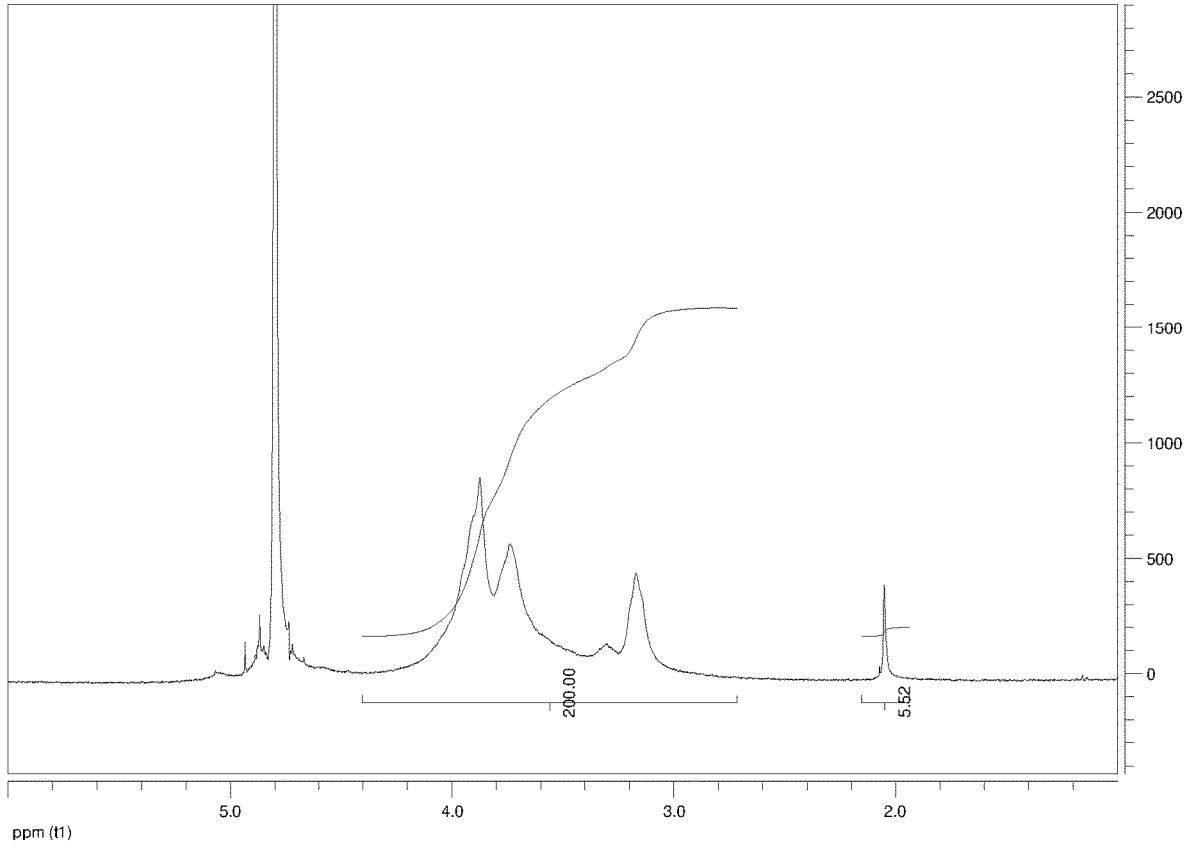
FIG. 5: 1H NMR spectrum obtained from chitosan deacetylated after a hydrolysis step applied to the commercial product.

Chitosan used as a starting material in the examples below was obtained in form of fine flakes from Chitinor (Norway). The degree of acetylation (DA) was determined by 1H NMR spectroscopy, as disclosed in Lavertu et al., "A validated 1H NMR method for the determination of the degree of deacetylation of chitosan", J Pharm Biomed Anal 2003, 32, 1149. Chitosan was analyzed in a mixture of 0.25% DCl in $D_2O$ at a chitosan concentration of approximately 0.5% (w/v). The spectra were recorded using a Bruker Avance III HD 300 spectrometer. The DA, calculated by comparing the integrated area under the peaks associated with H2-H6 of the D-glucosamine subunit with that of the methyl group, was determined as 15.9% for chitosan as purchased, and 5.5% for deacetylated chitosan obtained as disclosed in the following. FIG. 4 shows a 1H NMR spectrum obtained from this commercially available chitosan. FIG. 5 shows a corresponding 1H NMR spectrum obtained from chitosan deacetylated after a further hydrolysis step applied to the commercial product as described further below.

Deacetylation of Chitosan 50 g (grams) of chitosan flakes as obtained from the supplier Chitinor were placed in a glass container and 500 g of a 45% (w/v) aqueous sodium hydroxide solution were added. The glass container was well shaken to mix the components, and placed in an oven for 2 hours at 80° C. It was then removed from the oven and 500 ml (milliliters) of distilled water were added. The mixture was filtered through a 250 μm sieve. Then, chitosan was washed with distilled water until the pH of the filtrate reached approx. 6.5, and dried, resulting in chitosan having a DA of 5.5% as determined by 1H NMR spectroscopy (FIG. 5).

EXAMPLE 2

Preparation of a Film Supporting Structure Comprising Chitosan 7.5 g of chitosan having a degree of acetylation of 5% were dissolved in 500 ml of a 0.5% (w/v) aqueous acetic acid by gently shaking for 24 h.

144 ml of the chitosan solution was poured into a square-shaped mold, 24×24 cm² (square centimetres) in size, and left in a dust-free environment for drying at room temperature.

The dried film was placed for 2 hours in a bath containing a solution of 1.5% (w/v) ammonia in methanol/water 90/10 (v/v). The film was then removed from the bath and dried at room temperature. The resulting film has a content of approx. 100% (w/w) of chitosan, based on the non-aqueous components of the film. The remaining water content of the film is less than 10% (w/w). The film thickness is approx. 30 μm.

The film was mounted on a micropositioning stage, and a defined pattern of parallel grooves of approx. 10 μm in width separated by about 10 μm were micromachined on the film surface by using a custom-built 3D laser writing workstation with ultrashort (approx. 100 fs) laser pulses at a pulse repetition frequency of 80 MHz. Each line of a chevron pattern of grooves with a length of 125 μm and a V-angle of 120 degrees was made by a single pass of the laser at a constant speed of 50 μm/s.

The resulting film was then cut into 3×4 cm samples, placed in sterilization bags and sterilized using ethylene oxide.

Of course, without prejudice to the underlying principle, the embodiments and the details of construction may vary, even significantly, with respect to what has been illustrated herein purely by way of non-limiting example, without thereby departing from the extent of protection. The above extent of protection is defined by the annexed claims.

The invention claimed is:

1. A medical device having a film support structure, the film support structure comprising a composition containing chitosan, the film support structure further including a surface sculpturing, said surface sculpturing comprising a plurality of peaks and troughs defining a plurality of grooves, said peaks having a peak width ranging from 0.1 to 1000 μm, said troughs having a trough width ranging from 0.1 to 1000 μm, and wherein a distance between said peaks and said troughs ranges from 0.1 to 1000 μm, wherein the plurality of grooves of the surface sculpturing are arranged according to a chevron pattern, wherein the chevron pattern has a V-angle comprised between 90 and 120 degrees.

2. The medical device according to claim 1, wherein said peaks and said troughs have a length ranging from 1 to 100000 μm.

3. The medical device according to claim 1, wherein the thickness of the film support structure at said peak ranges from 0.2 to 2000 μm and the thickness of the film support structure at said trough ranges from 0.1 to 1000 μm.

4. The medical device according to claim 1, wherein the film support structure is a quadrangular film having a first dimension ranging from 1 to 100 mm and a second dimension ranging from 1 to 100 mm.

5. The medical device according to claim 1, wherein the chevron pattern has a band width of 100000 μm or less.

6. The medical device according to claim 1, wherein said composition comprises chitosan in an amount of at least 50% by weight based on the non-aqueous components of the composition.

7. The medical device according to claim 1, wherein said composition comprises a mixture of chitosan and at least one polymeric constituent.

8. The medical device according to claim 1, wherein said composition comprises at least one bioactive constituent.

9. The medical device according to claim 1, wherein said peaks and said troughs have a length ranging from 50 to 250 μm.

10. The medical device according to claim 1, wherein the film support structure is a quadrangular film having a first dimension ranging from 5 to 50 mm and a second dimension ranging from 5 to 50 mm.

11. The medical device according to claim 1, wherein the chevron pattern has a band width ranging from 50 to 250 μm.

12. The medical device according to claim 1, wherein said composition comprises a mixture of chitosan and at least one polymeric constituent selected from the group consisting of biodegradable polymers, biodissolvable polymers, copolymers, and mixtures thereof.

13. The medical device according to claim 1, wherein said composition comprises at least one bioactive constituent selected from the group consisting of proteins, peptides, nucleic acids, drugs, and mixtures thereof.

* * * * *